[54] 4-CARBAMOYLIMIDAZOLIUM-5-OLATE DERIVATIVES

[75] Inventors: Toshio Atsumi, Kawanishi; Yuzo Tarumi, Nishinomiya; Tetsutaro Sanjiki, Ibaraki; Yoshiaki Takebayashi, Toyonaka; Noboru Yoshida, Osaka, all of Japan

[73] Assignee: Sumitomo Chemical Company, Limited, Osaka, Japan

[21] Appl. No.: 366,423

[22] Filed: Apr. 7, 1982

[30] Foreign Application Priority Data

Apr. 20, 1981 [JP] Japan .................. 56-59930
Feb. 12, 1982 [JP] Japan .................. 57-21632

[51] Int. Cl.³ .................. C07H 17/02; A61K 31/70
[52] U.S. Cl. .................. 536/17.4; 424/180; 536/17.3
[58] Field of Search .................. 536/17.3, 17.4

[56] References Cited

U.S. PATENT DOCUMENTS

| | | | |
|---|---|---|---|
| 4,140,788 | 2/1979 | Atsumi et al. | 424/273 R |
| 4,218,457 | 8/1980 | Atsumi et al. | 424/273 R |
| 4,248,999 | 2/1981 | Baba et al. | 536/17.4 |
| 4,260,774 | 4/1981 | Atsumi et al. | 548/336 |
| 4,317,825 | 3/1982 | Atsumi et al. | 424/273 R |
| 4,332,806 | 6/1982 | Atsumi et al. | 424/273 R |

FOREIGN PATENT DOCUMENTS 539071 8/1973 Fed. Rep. of Germany ..... 536/17.4

OTHER PUBLICATIONS

Tarumi et al., Reprint from The Journal of Heterocyclic Chemistry, 17, (1425–1433), 1980.

*Primary Examiner*—Johnnie R. Brown
*Assistant Examiner*—Elli Peselev
*Attorney, Agent, or Firm*—Wenderoth, Lind & Ponack

[57] ABSTRACT

There are provided compounds of the formula:

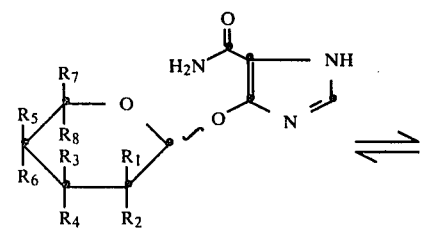

-continued

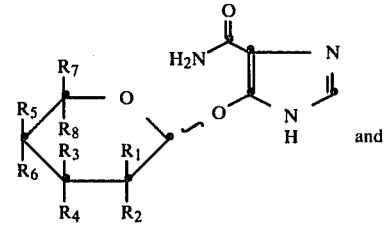

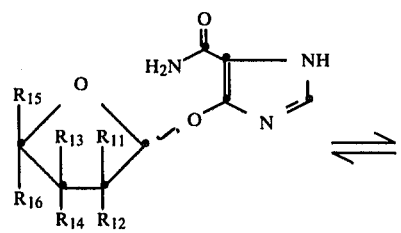

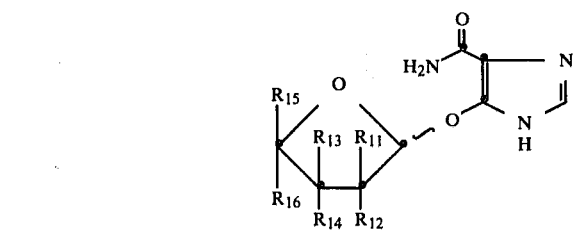

wherein either $R_1$ or $R_2$ is a hydrogen atom, a hydroxy group, an acyloxy group, a phthalimido group or an acetamido group and the other is a hydrogen atom; either $R_3$ or $R_4$ is a hydroxy group or an acyloxy group and the other is a hydrogen atom; either $R_5$ or $R_6$ is a hydroxy group or an acyloxy group and the other is a hydrogen atom; either $R_7$ or $R_8$ is a hydrogen atom, a methyl group, a hydroxymethyl group, an acyloxymethyl group, an alkoxycarbonyl group, a group of the formula:

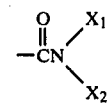

(wherein $X_1$ and $X_2$ are a hydrogen atom or a lower alkyl group), or a carboxyl group and the other is a hydrogen atom; either $R_{11}$ or $R_{12}$ is a hydrogen atom, a hydroxy group or an acyloxy group and the other is a hydrogen atom; either $R_{13}$ or $R_{14}$ is a hydroxy group or an acyloxy group and the other is a hydrogen atom; either $R_{15}$ or $R_{16}$ is a methyl group, a hydroxymethyl group or an acyloxymethyl group and the other is a hydrogen atom; and a process for producing them. These compounds are useful as antitumor agents.

22 Claims, No Drawings

4-CARBAMOYLIMIDAZOLIUM-5-OLATE DERIVATIVES

DESCRIPTION OF THE INVENTION

The present invention relates to novel 4-carbamoylimidazolium-5-olate derivatives and preparation thereof. More particularly, the present invention pertains to 4-carbamoylimidazolium-5-olate derivatives useful as antitumor agents, a pharmaceutical composition containing at least one of them and a process for preparing them.

It has been known that the compound of the following formula (II) has antitumor and immunosuppressive activity (Canada Pat. No. 1,078,736).

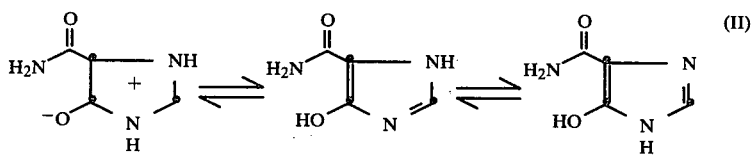

(II)

The compound of the formula (II) does not have necessarily sufficient solubility in aqueous media. Therefore, for use in therapy more soluble compounds are desired.

We have carried out an extensive study seeking new derivatives which have higher solubility in aqueous media and have now found the novel imidazole derivatives of the present invention.

The novel imidazole derivatives of the present invention are those represented by the following formula (I-a,b),

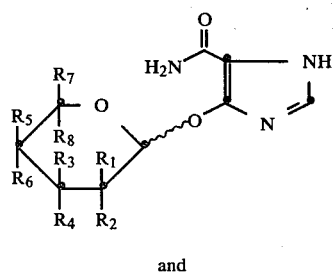

and

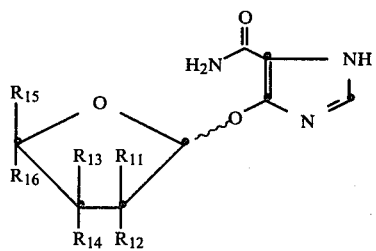

wherein either $R_1$ or $R_2$ is a hydrogen atom, a hydroxy group, an acyloxy group, a phthalimido group or an acetamido group and the other is a hydrogen atom; either $R_3$ or $R_4$ is a hydroxy group or an acyloxy group and the other is a hydrogen atom; either $R_5$ or $R_6$ is a hydroxy group or an acyloxy group and the other is a hydrogen atom; either $R_7$ or $R_8$ is a hydrogen atom, a methyl group, a hydroxymethyl group, an acyloxymethyl group, an alkoxycarbonyl group, a group of the formula:

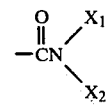

(wherein $X_1$ and $X_2$ are a hydrogen atom or a lower alkyl group), or a carboxyl group and the other is a hydrogen atom; either $R_{11}$ or $R_{12}$ is a hydrogen atom, a hydroxy group or an acyloxy group and the other is a hydrogen atom; either $R_{13}$ or $R_{14}$ is a hydroxy group or an acyloxy group and the other is a hydrogen atom; either $R_{15}$ or $R_{16}$ is a methyl group, a hydroxymethyl group or an acyloxymethyl group and the other is a hydrogen atom.

As used herein, the term "acyloxy" means lower alkanoyloxy having 2 to 7 carbon atoms (e.g. acetyloxy, propionyloxy, butyryloxy, isobutyryloxy, valeryloxy, isovaleryloxy, pivaloyloxy, hexanoyloxy, heptanoyloxy) and benzoyloxy which may be substituted with a lower alkyl group having 1 to 4 carbon atoms, a lower alkoxy group having 1 to 4 carbon atoms, a nitro group or a halogen atom as defined below (e.g. o-, m- or p-toluoyloxy, methoxybenzoyloxy, nitrobenzoyloxy). The term "acyloxymethyl" means methyl substituted with the above acyloxy group. The term "alkoxycarbonyl" means carbonyl substituted with a lower alkoxy group having 1 to 4 carbon atoms (e.g. methoxy, ethoxy, propoxy). The term "lower alkyl" in $X_1$ or $X_2$ means lower alkyl having 1 to 6 carbon atoms (e.g. methyl, ethyl, propyl).

The compound of the formula (I-a, b) of the present invention can be prepared by the following process. Thus, a 4-carbamoylimidazolium-5-olate derivative of the formula (III)

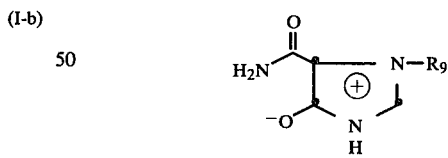

(III)

wherein $R_9$ is a hydrogen atom or a benzyl group which may be substituted with a nitro group, a lower alkyl group or a lower alkoxy group, or its reactive derivative is reacted with a carbohydrate derivative of the formula (IV-a, b)

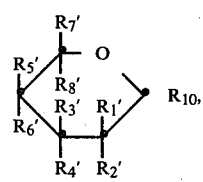

(IV-a)

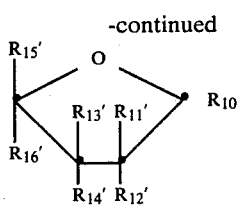

wherein either $R_1'$ or $R_2'$ is a hydrogen atom, an acyloxy group, a phthalimido group or an acetamido group and the other is a hydrogen atom; either $R_3'$ or $R_4'$ is an acyloxy group and the other is a hydrogen atom; either $R_5'$ or $R_6'$ is an acyloxy group and the other is a hydrogen atom; either $R_7'$ or $R_8'$ is a hydrogen atom, a methyl group, an acyloxymethyl group, an alkoxycarbonyl group or a group of the formula:

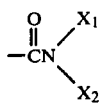

(wherein $X_1$ and $X_2$ are as defined above), and the other is a hydrogen atom; either $R_{11}'$ or $R_{12}'$ is a hydrogen atom or an acyloxy group and the other is a hydrogen atom; either $R_{13}'$ or $R_{14}'$ is an acyloxy group and the other is a hydrogen atom; either $R_{15}'$ or $R_{16}'$ is a methyl group or an acyloxymethyl group and the other is a hydrogen atom; $R_{10}$ is a halogen atom, a lower alkoxy group or a lower alkanoyloxy group, in the presence or absence of a Lewis acid to obtain a compound of the formula (V-a, b)

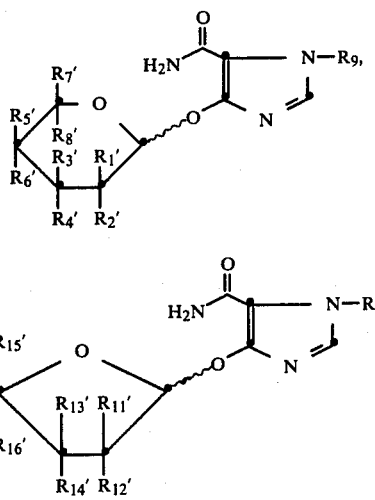

wherein $R_1'$, $R_2'$, $R_3'$, $R_4'$, $R_5'$, $R_6'$, $R_7'$, $R_8'$, $R_{11}'$, $R_{12}'$, $R_{13}'$, $R_{14}'$, $R_{15}'$, $R_{16}'$, $R_9$ are as defined above.

Examples of preferred reactive derivatives of the compound of the formula (III) are trialkyltin derivatives. The trialkyltin derivatives can be prepared, for example, by refluxing the compound of the formula (III) with bis(tributyltin)oxide in benzene for a few hours and evaporating the solvent under reduced pressure.

Typical examples of the Lewis acids are silver perchlorate, stannic chloride, zinc chloride, zinc bromide, titanium tetrachloride, silver trifluoromethanesulfonate and trimethylsilylperchlorate.

The term "substituted benzyl" means a benzyl substituted with one or two nitro groups, lower alkyl group having one to four carbon atoms or lower alkoxy group having one to four carbon atoms. The term "halogen" means fluorine, chlorine, bromine and iodine. Preferably chlorine and bromine can be used.

Examples of the carbohydrate derivatives of the formula (IV-a, b) are derivatives of D-glucose, L-glucose, D-galactose, D-mannose, L-mannose, D-glucosamine, D-galactosamine, D-mannosamine, L-rhamnose, D-fucose, L-fucose, D-glucuronic acid, 2-deoxy-D-glucose, 2-deoxy-D-galactose, D-ribofuranose, D-ribopyranose, D-xylofuranose, D-xylopyranose, D-arabinofuranose, D-arabinopyranose, D-lyxofuranose, D-lyxopyranose, L-xylofuranose, L-xylopyranose, L-arabinofuranose, L-arabinopyranose, L-lyxofuranose, L-luxopyranose, 2-deoxy-D-ribofuranose, 5-deoxy-D-ribofuranose, 5-deoxy-L-arabinose and the like.

Typical examples of preferred solvents which may be used in the reaction between the compound of the formula (III) and the compounds of the formula (IV-a, b) are ethers (e.g. tetrahydrofuran, dioxane, dimethoxyethane), polar solvents (e.g. acetonitrile, N,N-dimethylformamide, dimethylsulfoxide), hydrocarbon solvents (e.g. benzene, toluene, xylene), halogenated hydrocarbon solvents (e.g. carbon tetrachloride, dichloromethane, chloroform, 1,2-dichloroethane) and the like.

The reaction can generally be effected by controlling the reaction temperature at from $-70°$ to $50°$ C., preferably from $-20°$ to $25°$ C.

The compounds of the formula (V-a, b) can be isolated and purified by the known purification methods (e.g. recrystalization, column chromatography).

When $R_9$ is a benzyl group or its derivatives, the benzyl group which is a protective group of the compounds of the formula (V-a, b) can be removed by catalytic reduction in the presence or absence of the acid to obtain the compounds of the formula (I'-a, b)

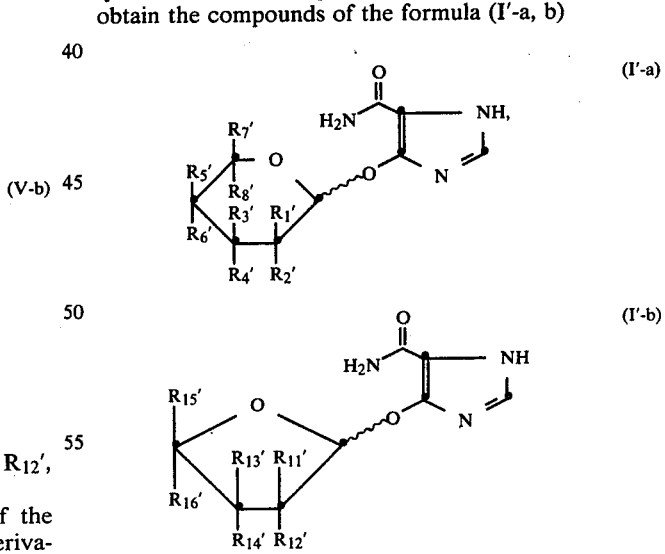

wherein $R_1'$, $R_2'$, $R_3'$, $R_4'$, $R_5'$, $R_6'$, $R_7'$, $R_8'$, $R_{11}'$, $R_{12}'$, $R_{13}'$, $R_{14}'$, $R_{15}'$, $R_{16}'$ are as defined above.

In this reaction, an example of a preferred benzyl group is a nitrobenzyl group, and the reaction can be accelerated by addition of 1 to 1.5 mol equivalents of the acids to finish the reaction in a few hours under atmospheric pressure. Typical examples of the acids are acetic acid, propionic acid, methanesulfonic acid, p-toluenesulfonic acid, hydrochloric acid, nitric acid and phosphoric acid. Typical examples of the catalyst which may be used in this reaction are palladium-carbon, palladium black, platinum oxide and Raney nickel.

Typical examples of the solvents which may be used in this reaction are ethers (e.g. tetrahydrofuran, dioxane), alcohols (e.g. methanol, ethanol) and water, preferably methanol containing water.

The protective group in the sugar moiety of the compounds of the formula (I'-a, b) can be removed by treating (I'-a, b) with methanol saturated with ammonia or metal alkoxide (e.g. sodium methoxide, sodium ethoxide) in alcohols (e.g. methanol, ethanol) to obtain the compounds of the formula (I''-a, b)

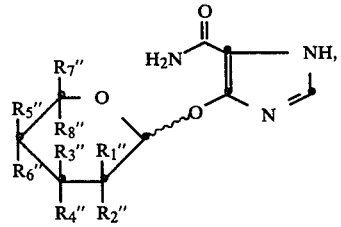

(I''-a)

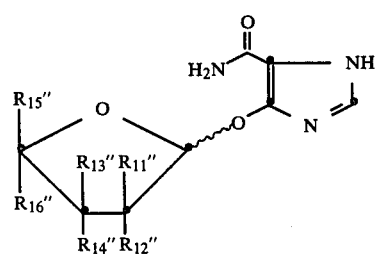

(I''-b)

wherein either $R_1''$ or $R_2''$ is a hydrogen atom, a hydroxy group, a phthalimido group or an acetamido group and the other is a hydrogen atom; either $R_3''$ or $R_4''$ is a hydroxy group and the other is a hydrogen atom; either $R_5''$ or $R_6''$ is a hydroxy group and the other is a hydrogen atom; either $R_7''$ or $R_8''$ is a hydrogen atom, a methyl group, a hydroxymethyl group, an alkoxycarbonyl group or a group of the formula:

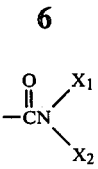

(wherein $X_1$ and $X_2$ are a hydrogen atom or a lower alkyl group) and the other is a hydrogen atom; either $R_{11}''$ or $R_{12}''$ is a hydrogen atom or a hydroxy group and the other is a hydrogen atom; either $R_{13}''$ or $R_{14}''$ is a hydroxy group and the other is a hydrogen atom; either $R_{15}''$ or $R_{16}''$ is a methyl group or a hydroxymethyl group and the other is a hydrogen atom.

The compound of the formula (I''-a) wherein either $R_7''$ or $R_8''$ is an alkoxycarbonyl group may be hydrolyzed to give a carboxyl derivative which may form a salt with a base (e.g. ammonia, triethylamine, sodium) or may produce the corresponding amide derivative by reaction with an organic amine (e.g. ammonia, methylamine, diethylamine).

The compounds of the formula (I-a, b) of the present invention may exist in a mixture of the two tautomers as follows:

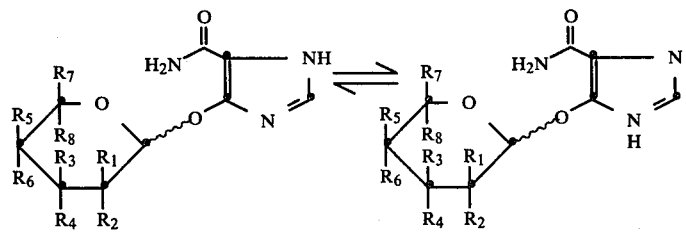

(I-a)

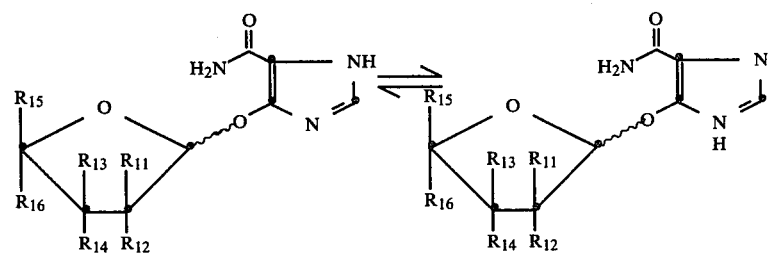

(I-b)

wherein $R_1$, $R_2$, $R_3$, $R_4$, $R_5$, $R_6$, $R_7$, $R_8$, $R_{11}$, $R_{12}$, $R_{13}$, $R_{14}$, $R_{15}$, $R_{16}$ are as defined above, both of which are within the scope of the present invention.

The compound of the formula (III) where $R_9$ is a benzyl group can be prepared by the following method.

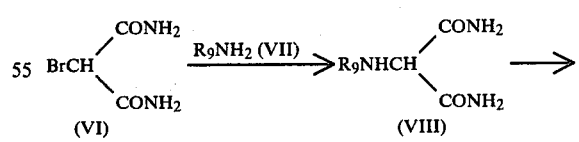

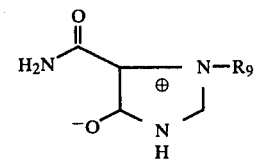

wherein $R_9$ is a benzyl group which may be substituted with a nitro group, a lower alkyl group or a lower alkoxy group.

The compounds of the present invention possess potent antitumor activities against Sarcoma 180, Lewis Lung Carcinoma, Ehrlich Carcinoma, P-388 leukemia and the like.

The compounds of the formula (I-a, b) are useful as antitumor agents and they exhibit particularly excellent inhibiting effects against tumors and prolongation effect on the life span.

The antitumor activities of the compounds of the present invention were estimated according to the methods described in "Cancer Chemotherapy Reports" Part 3, Vol. 3 (No. 2) p. 13 (1972).

The results are given in the following Table 1.

TABLE 1

Antitumor effect on mouse experimental tumors

| Compound | Dose (mg/kg) | Route | Schedule | Inhibition ratio (%) Lewis Lung Carcinoma (solid) |
|---|---|---|---|---|
| 4-(2,3,4,6-tetra-O—acetyl-β-D-glucopyranosyl)oxy-1H—imidazole-5-carboxamide | 360 180 90 | po po po | 9qd 9qd 9qd | 85 76 53 |
| 4-β-D-glucopyranosyloxy-1H—imidazole-5-carboxamide | 300 200 | ip ip | 9qd 9qd | 58 45 |
| 4-(2,3,4,6-tetra-O—acetyl-β-D-galactopyranosyl)oxy-1H—imidazole-5-carboxamide | 360 180 90 | po po po | 9qd 9qd 9qd | 89 84 58 |
| Methyl 1-O—(5-carbamoyl-1H—imidazole-4-yl)-2,3,4-tri-O—acetyl-β-D-glucopyranuronate | 175 87 | po po | 9qd 9qd | 55 53 |
| Methyl 1-O—(5-carbamoyl-1H—imidazole-4-yl)-β-D-glucopyranuronate | 200 | po | 9qd | 44 |
| 4-(2,3,5-tri-O—acetyl-β-D-ribofuranosyl)oxy-1H—imidazole-5-carboxamide | 50 100 | ip po | 9qd 9qd | 50 60 |
| 4-β-D-ribofuranosyloxy-1H—imidazole-5-carboxamide | 50 | ip | 9qd | 58.6 |
| 4-(2,3,4-tri-O—acetyl-α-L-rhamnopyranosyl)oxy-1H—imidazole-5-carboxamide | 314 157 | po po | 9qd 9qd | 66 43 |

BDF$_1$ male mice, 5 weeks old, weighing between 18 and 22 grams were used. Each test group was composed of 6 to 7 mice. Two million cells of Lewis Lung Carcinoma were injected in the hind leg. The drug was administered intraperitoneally or orally each day from 1 to 9 (or 9qd). After killing the mice at day 13, tumors were removed and weighed. The tumor inhibitory ratio was calculated according to the following formula.

$$\text{Inhibition ratio} = \left(1 - \frac{\text{the mean tumor weights of treated group}}{\text{the mean tumor weights of control group}}\right) \times 100$$

The compounds (I-a, b) of the present invention have low toxicity. They do not show any toxic symptoms, even when over 500 mg/kg of the compounds are orally administered to a mouse. Moreover, they do not exhibit an influence on decrease of peripheral leucocytes, which is one of the most serious side effects of immunosuppressants.

The compounds of the present invention can be administered orally or parenterally to a warm-blooded animal at a daily dose of 2–200 mg/kg as an antitumor agent, in a conventional dosage unit form.

The compounds of the present invention are made up alone or together with a conventional pharmaceutical carrier or diluent into a conventional solid or liquid pharmaceutical preparation (e.g. powders, granules, tablets, capsules, suspensions, emulsions, solutions) using the conventional methods in the pharmaceutical field. For example, tablets or capsules contain 50 to 500 mg of compounds (I-a, b). Especially, the compounds (I-a, b) of the present invention can be used for an injection, and as drops having water soluble property.

The following examples are shown to illustrate the present invention more precisely but it is not intended to limit the present invention thereto.

REFERENCE EXAMPLE 1

To a solution of 41.60 g of p-nitrobenzylamine in 660 ml of dry ethanol was added 49.34 g of α-bromomalonamide and 38.2 ml of triethylamine. After being stirred for two hours under refluxing, the reaction mixture was cooled to room temperature. And then separated crystals were filtered off, washed with ethanol and isopropyl ether, and dried to give 53.36 g of α-(4-nitrobenzyl)aminomalonamide. And a mixture of 50.45 g of α-(4-nitrobenzyl)aminomalonamide, 177.8 g of triethyl orthoformate and 0.76 g of p-toluenesulfonic acid monohydrate in 1.3 liters of dry ethanol was stirred for three hours under refluxing in an argon atmosphere. The reaction mixture was cooled on an ice-bath and separated crystals were filtered off, washed with ethanol and isopropyl ether, and dried to give 50.78 g of 5-carbamoyl-1-(4-nitrobenzyl)imidazolium-4-olate.

Crude material was recrystallized from 50% methanol-water, m.p. 266° C. (dec.).

$\nu_{max}^{nujol}$ (cm$^{-1}$): 3300, 3170, 3120, 1650, 1595, 1570, 1515

| Elemental analysis: | C (%) | H (%) | N (%) |
|---|---|---|---|
| Calculated for C$_{11}$H$_{10}$N$_4$O$_4$·½H$_2$O | 48.71 | 4.09 | 20.66 |
| Found | 48.91 | 4.03 | 20.77 |

EXAMPLE 1

To a solution of 2.570 g of silver trifluoromethanesulfonate, dried under reduced pressure, in 40 ml of dry nitromethane was added 1.35 ml of tetramethylurea. A solution of 4.112 g of 2,3,4,6-tetra-O-acetyl-α-D-glucopyranosyl bromide in 15 ml of dry nitromethane was added to the reaction mixture at a temperature from 0° C. to −15° C. After being stirred for 15 minutes, the reaction mixture was cooled on an ice-salt bath (at a temperature −11° C.) and 25 ml of benzene solution of tributyltin derivative of 1.311 g of 5-carbamoyl-1-(4-nitrobenzyl)imidazolium-4-olate which was prepared by refluxing a mixture of 5-carbamoyl-1-(4-nitrobenzyl)imidazolium-4-olate and bis-(tri-n-butyltin)oxide in dry benzene, was added. After being stirred for an hour, the reaction mixture was gradually heated up to room temperature and the stirring was continued for 17 hours. The separated crystals were filtered off, and washed with dry benzene. The filtrate was concentrated under reduced pressure to give 11.43 g of oily residue, which was purified by silica gel column chromatography eluted with a mixture of methylene chloride and acetone (=5/1) and there was obtained 2.744 g of 1-(4-nitrobenzyl)-4-(2,3,4,6-tetra-o-acetyl-$\beta$-D-glucopyranosyl)oxy-1H-imidazole-5-carboxamide.

Crude material was recrystallized from ethanol-isopropyl ether-n-hexane. m.p. 100°–102° C.

| Elemental analysis | C (%) | H (%) | N (%) |
| --- | --- | --- | --- |
| Calculated for $C_{25}H_{28}N_4O_{13}.\frac{1}{2}H_2O$ | 49.92 | 4.86 | 9.32 |
| Found | 50.12 | 4.81 | 9.23 |

$\nu_{max}^{nujol}$ (cm$^{-1}$): 3460, 3350, 3170, 3110, 1750, 1660, 1600

EXAMPLE 2

To a solution of 0.150 g of 1-(4-nitrobenzyl)-4-(2,3,4,6-tetra-O-acetyl-$\beta$-D-glucopyranosyl)oxy-1H-imidazole-5-carboxamide in 10 ml of tetrahydrofuran were added 0.3 ml of N-HCl aqueous solution and 80 mg of 10% palladium-carbon and a catalytic reduction was continued for an hour. To the reaction mixture was added 250 mg of sodium bicarbonate, and it was stirred for half an hour.

Separated crystals were filtered off and the filtrate was concentrated under reduced pressure. Chromatographical purification on silica gel in chloroform-methanol mixture (15:1) of the residue gave 92 mg of 4-(2,3,4,6-tetra-O-acetyl-$\beta$-D-glucopyranosyl)oxy-1H-imidazole-5-carboxamide, which was recrystallized from ethanol-isopropyl ether to give colorless needle crystals. m.p. 237°–238° C.

| Elemental analysis | C (%) | H (%) | N (%) |
| --- | --- | --- | --- |
| Calculated for $C_{18}H_{23}N_3O_{11}.H_2O$ | 45.47 | 5.30 | 8.84 |
| Found | 45.75 | 5.04 | 8.48 |

$\nu_{max}^{nujol}$ (cm$^{-1}$): 3490, 3340, 3140, 1750, 1665, 1650, 1605

$\lambda$max in water 248 nm ($\epsilon$ 13500)
$\lambda$max in N-HCl aqueous solution 231 nm ($\epsilon$ 9000)
$\lambda$max in N-NaOH aqueous solution 264 nm ($\epsilon$ 14500)

EXAMPLE 3

To a solution of 457 mg of 4-(2,3,4,6-tetra-O-acetyl-$\beta$-D-glucopyranosyl)oxy-1H-imidazole-5-carboxamide in 30 ml of dry methanol was added 270 mg of 95% sodium methoxide. The reaction mixture was stirred for 20 minutes at room temperature and 0.33 ml of acetic acid was added. Chromatographical purification on LH-20 (product of Pharmacia A/S) in methanol of the residue which was obtained after evaporation of the reaction mixture under reduced pressure, gave 260 mg of 4-$\beta$-D-glucopyranosyloxy-1H-imidazole-5-carboxamide which was crystallized with acetone. m.p. 167° C. (dec.)

| Elemental analysis: | C (%) | H (%) | N (%) |
| --- | --- | --- | --- |
| Calculated for $C_{10}H_{15}N_3O_7.\frac{1}{2}H_2O$ | 40.27 | 5.41 | 14.09 |
| Found | 40.38 | 5.43 | 13.97 |

$\nu_{max}^{KBr}$ (cm$^{-1}$): 3430, 3320, 3200, 2910, 1675, 1610
$\lambda$max in water 248 nm ($\epsilon$ 11800)
$\lambda$max in N-HCl aqueous solution 241 nm ($\epsilon$ 8400)
$\lambda$max in N-NaOH aqueous solution 265 nm ($\epsilon$ 12500)

EXAMPLE 4

Following a procedure similar to that of Example 1 but using 2.622 g of 5-carbamoyl-1-(4-nitrobenzyl)imidazolium-4-olate and 8.220 g of 2,3,4,6-tetra-O-acetyl-$\alpha$-D-galactopyranosyl bromide there was obtained 3.857 g of 1-(4-nitrobenzyl)-4-(2,3,4,6-tetra-O-acetyl-$\beta$-D-galactopyranosyl)oxy-1H-imidazole-5-carboxamide.

Recrystallization from ethanol-isopropyl ether-n-hexane. m.p. 111° C. (dec.)

$\nu_{max}^{nujol}$ (cm$^{-1}$): 3450, 3350, 1755, 1655, 1600, 1350, 1245, 1225, 1080, 1025, 960, 735

| Elemental analysis: | C (%) | H (%) | N (%) |
| --- | --- | --- | --- |
| Calculated for $C_{25}H_{28}N_4O_{13}.0.5H_2O$ | 49.92 | 4.86 | 9.32 |
| Found | 49.85 | 4.90 | 9.02 |

EXAMPLE 5

Following a procedure similar to that of Example 2 but using 2.664 g of 1-(4-nitrobenzyl)-4-(2,3,4,6-tetra-O-acetyl-$\beta$-D-galactopyranosyl)oxy-1H-imidazole-5-carboxamide there was obtained 1.90 g of 4-(2,3,4,6-tetra-O-acetyl-$\beta$-D-galactopyranosyl)oxy-1H-imidazole-5-carboxamide. m.p. 234.5°–235° C.

$\nu_{max}^{nujol}$ (cm$^{-1}$): 3460, 3150, 1750, 1660, 1610, 1505, 1430, 1215, 1070, 1035, 915, 690

| Elemental analysis: | C (%) | H (%) | N (%) |
| --- | --- | --- | --- |
| Calculated for $C_{18}H_{23}N_3O_{11}.\frac{1}{2}H_2O$ | 46.80 | 5.13 | 9.10 |
| Found | 46.89 | 5.10 | 9.15 |

EXAMPLE 6

Following a procedure similar to that of Example 3 but using 1.143 g of 4-(2,3,4,6-tetra-O-acetyl-$\beta$-D-galactopyranosyl)oxy-1H-imidazole-5-carboxamide there was obtained 0.570 g of 4-$\beta$-D-galactopyranosyloxy-1H-imidazole-5-carboxamide. m.p. 130° C.

$\nu_{max}^{KBr}$ (cm$^{-1}$): 3350, 2920, 1655, 1605, 1500, 1430, 1330, 1115, 1065, 1020

| Elemental analysis: | C (%) | H (%) | N (%) |
| --- | --- | --- | --- |
| Calculated for $C_{10}H_{15}N_3O_7.\frac{1}{2}MeOH.\frac{1}{2}H_2O$ | 40.13 | 5.77 | 13.37 |
| Found | 39.90 | 5.68 | 13.33 |

EXAMPLE 7

Following a procedure similar to that of Example 1 but using 1.311 g of 5-carbamoyl-1-(4-nitrobenzyl)imidazolium-4-olate and 3.658 g of 2-acetamido-3,4,6-tri-O-acetyl-2-deoxy-$\alpha$-D-glucopyranosyl chloride there was obtained 1.0 g of 1-(4-nitrobenzyl)-4-(2- acetamido-3,4,6-tri-O-acetyl-2-deoxy-β-D-glucopyranosyl)oxy-1H-imidazole-5-carboxamide.

Recrystallization from methanol-isopropyl ether-n-hexane. m.p. 114°–117° C.

$v_{max}^{KBr}$ (cm$^{-1}$): 3450, 1750, 1650, 1600, 1520, 1470, 1370, 1345, 1230, 1050

| Elemental analysis: | C (%) | H (%) | N (%) |
|---|---|---|---|
| Calculated for C$_{25}$H$_{29}$N$_5$O$_{12}$.1.2H$_2$O | 48.97 | 5.16 | 11.42 |
| Found | 49.29 | 5.01 | 11.05 |

EXAMPLE 8

Following a procedure similar to that of Example 2 but using 0.861 g of 1-(4-nitrobenzyl)-4-(2-acetamido-3,4,6-tri-O-acetyl-2-deoxy-β-D-glucopyranosyl)-oxy-1H-imidazole-5-carboxamide there was obtained 0.523 g of 4-(2-acetamido-3,4,6-tri-O-acetyl-2-deoxy-β-D-glucopyranosyl)oxy-1H-imidazole-5-carboxamide.

Recrystallization from chloroform-ether. m.p. 133°–135° C.

$v_{max}^{KBr}$ (cm$^{-1}$): 3450, 1750, 1650, 1600, 1240, 1040

| Elemental analysis: | C (%) | H (%) | N (%) |
|---|---|---|---|
| Calculated for C$_{18}$H$_{24}$N$_4$O$_{10}$.1.0H$_2$O | 45.57 | 5.52 | 11.81 |
| Found | 45.82 | 5.40 | 11.43 |

EXAMPLE 9

Following a procedure similar to that of Example 3 but using 0.107 g of 4-(2-acetamido-3,4,6-tri-O-acetyl-2-deoxy-β-D-glucopyranosyl)oxy-1H-imidazole-5-carboxamide there was obtained 0.076 g of 4-(2-acetamido-2-deoxy-β-D-glucopyranosyl)oxy-1H-imidazole-5-carboxamide. m.p. 140° C. (dec.)

$v_{max}^{nujol}$ (cm$^{-1}$): 3440, 1640, 1600, 1500, 1330, 1110, 1065, 1010

EXAMPLE 10

Following a procedure similar to that of Example 1 but using 2.88 g of 5-carbamoyl-1-(4-nitrobenzyl)imidazolium-4-olate and 7.77 g of 2,3,4-tri-O-acetyl-α-L-rhamnopyranosyl bromide there was obtained 3.32 g of 1-(4-nitrobenzyl)-4-(2,3,4-tri-O-acetyl-α-L-rhamnopyranosyl)oxy-1H-imidazole-5-carboxamide.

Recrystallization from chloroform-n-hexane. m.p. 103°–105° C.

$v_{max}^{nujol}$ (cm$^{-1}$): 3475, 1750, 1660, 1600, 1520, 1440, 1240, 1220, 1050, 960

| Elemental analysis: | C (%) | H (%) | N (%) |
|---|---|---|---|
| Calculated for C$_{23}$H$_{26}$N$_4$O$_{11}$.0.3H$_2$O | 51.17 | 4.97 | 10.38 |
| Found | 51.59 | 5.07 | 10.03 |

EXAMPLE 11

Following a procedure similar to that of Example 2 but using 1.728 g of 1-(4-nitrobenzyl)-4-(2,3,4-tri-O-acetyl-α-L-rhamnopyranosyl)oxy-1H-imidazole-5-carboxamide there was obtained 1.258 g of 4-(2,3,4-tri-O-acetyl-α-L-rhamnopyranosyl)oxy-1H-imidazole-5-carboxamide.

Recrystallization from chloroform-n-hexane. m.p. 183.5°–185.5° C.

$v_{max}^{nujol}$ (cm$^{-1}$): 3460, 3170, 1750, 1650, 1600, 1240, 1220

| Elemental analysis: | C (%) | H (%) | N (%) |
|---|---|---|---|
| Calculated for C$_{16}$H$_{21}$N$_3$O$_9$.0.2H$_2$O | 47.69 | 5.35 | 10.43 |
| Found | 47.57 | 5.38 | 10.30 |

EXAMPLE 12

Following a procedure similar to that of Example 3 but using 1.03 g of 4-(2,3,4-tri-O-acetyl-α-L-rhamnopyranosyl)oxy-1H-imidazole-5-carboxamide there was obtained 0.623 g of 4-α-L-rhamnopyranosyloxy-1H-imidazole-5-carboxamide. m.p. 115° C. (dec.)

$v_{max}^{nujol}$ (cm$^{-1}$): 3460, 3400–3050, 1650, 1600, 1500, 1330, 1140, 1115, 1060, 960

| Elemental analysis: | C (%) | H (%) | N (%) |
|---|---|---|---|
| Calculated for C$_{10}$H$_{15}$N$_3$O$_6$.0.5H$_2$O | 42.55 | 5.71 | 14.89 |
| Found | 42.77 | 5.78 | 14.87 |

EXAMPLE 13

Following a procedure similar to that of Example 1 but using 1.017 g of 4-carbamoyl-imidazolium-5-olate and 2,3,5-tri-O-benzoyl-D-arabinofuranosyl bromide there was obtained 0.9 g of 4-(2,3,5-tri-O-benzyl-α-D-arabinofuranosyl)oxy-1H-imidazole-5-carboxamide.

Recrystallization from chloroform-ether. m.p. 215°–216° C.

$v_{max}^{nujol}$ (cm$^{-1}$): 3460, 3360, 1720, 1665, 1610, 1280, 1120, 980, 705

| Elemental analysis: | C (%) | H (%) | N (%) |
|---|---|---|---|
| Calculated for C$_{30}$H$_{25}$N$_3$O$_9$ | 63.05 | 4.41 | 7.35 |
| Found | 62.74 | 4.43 | 7.22 |

EXAMPLE 14

Following a procedure similar to that of Example 3 but using 0.114 g of 4-(2,3,5-tri-O-benzoyl-α-D-arabinofuranosyl)oxy-1H-imidazole-5-carboxamide there was obtained 0.045 g of 4-α-D-arabinofuranosyloxy-1H-imidazole-5-carboxamide. m.p. 80° C.

$v_{max}^{nujol}$ (cm$^{-1}$): 3450–3150, 1650, 1600, 1110, 1070, 960

| Elemental analysis: | C (%) | H (%) | N (%) |
|---|---|---|---|
| Calculated for C$_9$H$_{13}$N$_3$O$_6$.1.1H$_2$O | 38.74 | 5.49 | 15.06 |
| Found | 38.65 | 5.13 | 14.78 |

EXAMPLE 15

Following a procedure similar to that of Example 1 but using 4-carbamoyl-imidazolium-5-olate and 2,3,4,6-tetra-O-acetyl-α-D-glucopyranosyl bromide there was obtained 4-(2,3,4,6-tetra-O-acetyl-β-D-glucopyranosyl- )oxy-1H-imidazole-5-carboxamide. This product was identified to be same as that obtained in Example 2.

EXAMPLE 16

Following a procedure similar to that of Example 1 but using 4-carbamoyl-imidazolium-5-olate and 2,3,4,6-tetra-O-acetyl-α-D-mannopyranosyl chloride there was obtained 4-(2,3,4,6-tetra-O-acetyl-α-D-mannopyranosyl)oxy-1H-imidazole-5-carboxamide. m.p. 148°–154° C. (92° C. sintering)

$\nu_{max}^{nujol}$ (cm$^{-1}$): 3460, 3150, 1750, 1645, 1595

| Elemental analysis: | C (%) | H (%) | N (%) |
|---|---|---|---|
| Calculated for $C_{18}H_{23}N_3O_{11}\cdot2H_2O$ | 43.81 | 5.51 | 8.52 |
| Found | 43.45 | 4.97 | 7.94 |

EXAMPLE 17

Following a procedure similar to that of Example 1 but using 4-carbamoyl-imidazolium-5-olate and 3,4,6-tri-O-acetyl-2-deoxy-2-phthalimido-β-D-glucopyranosyl chloride there was obtained 4-(3,4,6-tri-O-acetyl-2-deoxy-2-phthalimido-β-D-glucopyranosyl)oxy-1H-imidazole-5-carboxamide. m.p. 202°–208° C.

$\nu_{max}^{nujol}$ (cm$^{-1}$): 3460, 3270, 1780, 1750, 1735, 1710, 1665, 1600

| Elemental analysis: | C (%) | H (%) | N (%) |
|---|---|---|---|
| Calculated for $C_{24}H_{24}N_4O_{10}\cdot2H_2O$ | 51.06 | 5.00 | 9.93 |
| Found | 51.23 | 4.48 | 9.72 |

EXAMPLE 18

Following a procedure similar to that of Example 1 but using 1.442 g of 5-carbamoyl-1-(4-nitrobenzyl)imidazolium-4-olate and 4.37 g of methyl 1-bromo-1-deoxy-2,3,4-tri-O-acetyl-α-D-glucopyranuronate there was obtained methyl 1-O-[5-carbamoyl-1-(4-nitrobenzyl)imidazole-4-yl]-2,3,4-tri-O-acetyl-β-D-glucopyranuronate. The resulting product as such was used as the starting compound in the following Example 19.

EXAMPLE 19

Following a procedure similar to that of Example 2 but using 1.157 g of methyl 1-O-[5-carbamoyl-1-(4-nitrobenzyl)imidazole-4-yl]-2,3,4-tri-O-acetyl-β-D-glucopyranuronate there was obtained 0.825 g of methyl 1-O-(5-carbamoyl-1H-imidazole-4-yl)-2,3,4-tri-O-acetyl-β-D-glucopyranuronate. m.p. 211°–212° C.

$\nu_{max}^{nujol}$ (cm$^{-1}$): 3450, 3350, 3175, 1760, 1655, 1605, 1500, 1440, 1220, 1100, 1040

EXAMPLE 20

Following a procedure similar to that of Example 3 but using 0.85 g of methyl 1-O-(5-carbamoyl-1H-imidazole-4-yl)-2,3,4-tri-O-acetyl-β-D-glucopyranuronate there was obtained 0.55 g of methyl 1-O-(5-carbamoyl-1H-imidazole-4-yl)-β-D-glucopyranuronate. m.p. 146° C. (dec.)

$\nu_{max}^{nujol}$ (cm$^{-1}$): 3450, 3330, 1740, 1650, 1600, 1085, 1020

| Elemental analysis: | C (%) | H (%) | N (%) |
|---|---|---|---|
| Calculated for $C_{11}H_{15}N_3O_8\cdot\frac{3}{4}H_2O$ | 39.94 | 5.03 | 12.70 |
| Found | 40.12 | 4.80 | 12.13 |

EXAMPLE 21

A solution of 0.55 g of methyl 1-O-(5-carbamoyl-1H-imidazole-4-yl)-β-D-glucopyranuronate in 50 ml of dry methanol was saturated with ammonia (gas) cooling in an ice bath and the reaction mixture was stirred for 1.5 hours. Then the reaction mixture was heated to room temperature and was concentrated to a residue under reduced pressure. The residue was washed with methanol and ether, and then separated crystals were filtered off and dried to give 0.5 g of 1-O-(5-carbamoyl-1H-imidazole-4-yl)-β-D-glucopyranuronamide which was recrystallized from water-ethanol. m.p. 206° C. (dec.)

$\nu_{max}^{nujol}$ (cm$^{-1}$): 3590, 3410, 3170, 1690, 1660, 1610, 1340, 1155, 1070, 1040, 1025, 1010, 800, 790

| Elemental analysis: | C (%) | H (%) | N (%) |
|---|---|---|---|
| Calculated $C_{10}H_{14}N_4O_7\cdot1H_2O$ | 37.50 | 5.04 | 17.49 |
| Found | 37.43 | 5.14 | 17.55 |

EXAMPLE 22

A solution of 0.635 g of methyl 1-O-(5-carbamoyl-1H-imidazole-4-yl)-β-D-glucopyranuronate in 20 ml of dry methanol was saturated with methylamine (gas) cooling in an ice bath and the reaction mixture was stirred for 2 hours. Separated crystals were filtered off and dried to give 0.6 g of N-methyl[1-O-(5-carbamoyl-1H-imidazole-4-yl)-β-D-glucopyran]uronamide which was recrystallized from water-n-propanol. m.p. 168° C. (dec.)

$\nu_{max}^{nujol}$ (cm$^{-1}$): 3490, 3450, 3350, 3250, 1660, 1640, 1610, 1515, 1440, 1420, 1170, 1130, 1110, 1085, 1070, 1020, 770

| Elemental analysis: | C (%) | H (%) | N (%) |
|---|---|---|---|
| Calculated for $C_{11}H_{16}N_4O_7\cdot1H_2O$ | 39.52 | 5.43 | 16.76 |
| Found | 39.28 | 5.41 | 16.55 |

EXAMPLE 23

A solution of 0.635 g of methyl 1-O-(5-carbamoyl-1H-imidazole-4-yl)-β-D-glucopyranuronate in 12 ml of methanol, 7.4 ml of water and 0.6 ml of 28%-ammonia water was stirred for 24 hours at room temperature. The reaction mixture was concentrated to a residue under reduced pressure below 40° C. and the residue was crystallized with methanol giving 0.5 g of ammonium 1-O-(5-carbamoyl-1H-imidazole-4-yl)-β-D-glucopyranuronate which was recrystallized from water-methanol. m.p. 185° C. (dec.)

$\nu_{max}^{nujol}$ (cm$^{-1}$): 3440, 3400, 3330, 3280, 3220, 1660, 1620, 1580, 1515, 1400, 1100, 1070, 1040, 1020

| Elemental analysis: | C (%) | H (%) | N (%) |
|---|---|---|---|
| Calculated for | 37.50 | 5.04 | 17.49 |

-continued

| Elemental analysis: | C (%) | H (%) | N (%) |
|---|---|---|---|
| $C_{10}H_{16}N_4O_8$ | | | |
| Found | 37.69 | 5.27 | 16.96 |

EXAMPLE 24

Following a procedure similar to that of Example 1 but using 2,3,5-tri-O-acetyl-D-ribofuranosyl chloride prepared from 2.50 g of 1,2,3,5-tetra-O-acetyl-$\beta$-D-ribofuranose and 1.022 g of 5-carbamoyl-1-(4-nitrobenzyl)imidazolium-4-olate there was obtained 0.986 g of 1-(4-nitrobenzyl)-4-(2,3,5-tri-O-acetyl-$\beta$-D-ribofuranosyl)oxy-1H-imidazole-5-carboxamide which was recrystallized from ethanol. m.p. 155.5°–156.5° C.

| Elemental analysis: | C (%) | H (%) | N (%) |
|---|---|---|---|
| Calculated for $C_{22}H_{24}N_4O_{11}\cdot\frac{1}{2}H_2O$ | 49.90 | 4.76 | 10.58 |
| Found | 50.09 | 4.63 | 10.60 |

EXAMPLE 25

Following a procedure similar to that of Example 2 but using 3.360 g of 1-(4-nitrobenzyl)-4-(2,3,5-tri-O-acetyl-$\beta$-D-ribofuranosyl)oxy-1H-imidazole-5-carboxamide there was obtained 1.829 g of 4-(2,3,5-tri-O-acetyl-$\beta$-D-ribofuranosyl)oxy-1H-imidazole-5-carboxamide which was recrystallized from chloroform-isopropyl ether. m.p. 132°–133.5° C.

$\nu_{max}^{nujol}$ (cm$^{-1}$): 3470, 3320, 3150, 1745, 1650, 1600, 1570

| Elemental analysis: | C (%) | H (%) | N (%) |
|---|---|---|---|
| Calculated for $C_{15}H_{19}N_3O_9$ | 46.75 | 4.97 | 10.91 |
| Found | 46.54 | 5.08 | 10.58 |

$\lambda_{max}$ in water 250 nm ($\epsilon$ 13400)
$\lambda_{max}$ in N-HCl aqueous solution 241 nm ($\epsilon$ 9700)
$\lambda_{max}$ in N-NaOH aqueous solution 265 nm ($\epsilon$ 13300)

EXAMPLE 26

Following a procedure similar to that of Example 3 but using 1.156 g of 4-(2,3,5-tri-O-acetyl-$\beta$-D-ribofuranosyl)oxy-1H-imidazole-5-carboxamide there was obtained 0.724 g of 4-$\beta$-D-ribofuranosyloxy-1H-imidazole-5-carboxamide. m.p. 167° C. (dec.)

$\nu_{max}^{KBr}$ (cm$^{-1}$): 3450, 3350, 3260, 1670, 1595, 1505

| Elemental analysis: | C (%) | H (%) | N (%) |
|---|---|---|---|
| Calculated for $C_9H_{13}N_3O_6\cdot 3/5H_2O$ | 40.03 | 5.30 | 15.56 |
| Found | 39.62 | 4.90 | 15.35 |

$\lambda_{max}$ in water 251 nm ($\epsilon$ 11800)
$\lambda_{max}$ in N-HCl aqueous solution 242 nm ($\epsilon$ 8100)
$\lambda_{max}$ in N-NaOH aqueous solution 265 nm ($\epsilon$ 11600)

According to the present invention, there are obtained, for example, the following compounds:

4-(2,3,5-tri-O-benzoyl-$\beta$-D-ribofuranosyl)oxy-1H-imidazole-5-carboxamide
4-$\alpha$-D-mannopyranosyloxy-1H-imidazole-5-carboxamide
1-O-(5-carbamoyl-1H-imidazole-4-yl)-$\beta$-D-glucopyranuronic acid
4-(2-deoxy-2-phthalimido-$\beta$-D-glucopyranosyl)oxy-1H-imidazole-5-carboxamide
4-(2,3,4-tri-O-acetyl-$\beta$-D-ribopyranosyl)oxy-1H-imidazole-5-carboxamide
4-$\beta$-D-ribopyranosyloxy-1H-imidazole-5-carboxamide
4-(2,3,5-tri-O-acetyl-$\beta$-D-xylofuranosyl)oxy-1H-imidazole-5-carboxamide
4-$\beta$-D-xylofuranosyloxy-1H-imidazole-5-carboxamide
4-(2,3,4-tri-O-acetyl-$\beta$-D-xylopyranosyl)oxy-1H-imidazole-5-carboxamide
4-$\beta$-D-xylopyranosyl-1H-imidazole-5-carboxamide
4-(2,3,4-tri-O-acetyl-$\alpha$-D-arabinopyranosyl)oxy-1H-imidazole-5-carboxamide
4-$\alpha$-D-arabinopyranosyloxy-1H-imidazole-5-carboxamide
4-(2,3,5-tri-O-acetyl-$\alpha$-D-lyxofuranosyl)oxy-1H-imidazole-5-carboxamide
4-$\alpha$-D-lyxofuranosyloxy-1H-imidazole-5-carboxamide
4-(2,3,4-tri-O-acetyl-$\alpha$-D-lyxopyranosyl)oxy-1H-imidazole-5-carboxamide
4-$\alpha$-D-lyxopyranosyloxy-1H-imdazole-5-carboxamide
4-(2-deoxy-3,5-di-O-p-nitrobenzoyl-$\alpha$-D-ribofuranosyl)oxy-1H-imidazole-5-carboxamide
4-(2-deoxy-3,5-di-O-p-nitrobenzoyl-$\beta$-D-ribofuranosyl)oxy-1H-imidazole-5-carboxamide
4-(2-deoxy-$\alpha$-D-ribofuranosyl)oxy-1H-imidazole-5-carboxamide
4-(2-deoxy-$\beta$-D-ribofuranosyl)oxy-1H-imidazole-5-carboxamide
4-(2,3-di-O-acetyl-5-deoxy-$\beta$-D-ribofuranosyl)oxy-1H-imidazole-5-carboxamide
4-(5-deoxy-$\beta$-D-ribofuranosyl)oxy-1H-imidazole-5-carboxamide

What is claimed is:
1. A compound selected from the group consisting of compounds of the formulae:

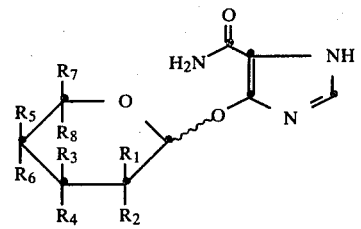

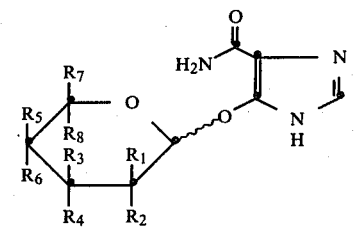

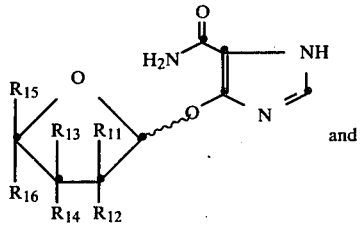

and

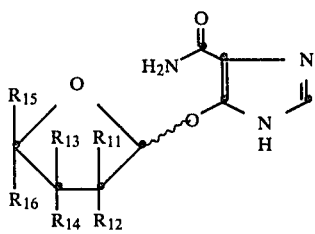

wherein one of $R_1$ and $R_2$ is selected from the group consisting of hydrogen, hydroxy, acyloxy, phthalimido and acetamido and the other is hydrogen; one of $R_3$ and $R_4$ is selected from the group consisting of hydroxy and acyloxy and the other is hydrogen; one of $R_5$ and $R_6$ is selected from the group consisting of hydroxy and acyloxy and the other is hydrogen; one of $R_7$ and $R_8$ is selected from the group consisting of hydrogen, methyl, hydroxymethyl, acyloxymethyl, alkoxycarbonyl of 1 to 4 carbon atoms in the alkoxy group, a group of the formula:

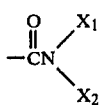

(wherein $X_1$ and $X_2$ are selected from the group consisting of hydrogen and alkyl of 1 to 6 carbon atoms) and carboxyl and the other is hydrogen; one of $R_{11}$ and $R_{12}$ is selected from the group consisting of hydrogen, hydroxy and acyloxy and the other is hydrogen; one of $R_{13}$ and $R_{14}$ is selected from the group consisting of hydroxy and acyloxy and the other is hydrogen; one of $R_{15}$ and $R_{16}$ is selected from the group consisting of methyl, hydroxymethyl and acyloxymethyl and the other is hydrogen, wherein all of said acyloxy groups, including the acyloxy groups of said acyloxymethyl groups, are selected from the group consisting of alkanoyloxy of 2 to 7 carbon atoms and benzoyloxy, said benzoyloxy being unsubstituted or substituted by a member selected from the group consisting of alkyl of 1 to 4 carbon atoms, alkoxy of 1 to 4 carbon atoms, nitro and halogen.

2. A compound according to claim 1 which is selected from the group consisting of compounds of the formulae:

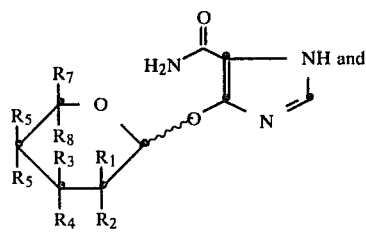

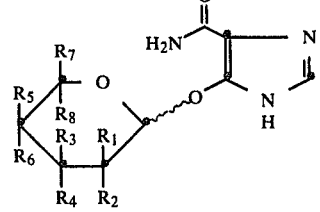

wherein $R_1$, $R_2$, $R_3$, $R_4$, $R_5$, $R_6$, $R_7$ and $R_8$ are as defined in claim 1.

3. A compound according to claim 1 which is selected from the group consisting of compounds of the formulae:

wherein $R_{11}$, $R_{12}$, $R_{13}$, $R_{14}$, $R_{15}$ and $R_{16}$ are as defined in claim 1.

4. 4-(2,3,4,6-tetra-O-acetyl-β-D-glucopyranosyl)oxy-1H-imidazole-5-carboxamide.
5. 4-β-D-glucopyranosyloxy-1H-imidazole-5-carboxamide.
6. 4-(2,3,4,6-tetra-O-acetyl-β-D-galactopyranosyl)oxy-1H-imidazole-5-carboxamide.
7. 4-β-D-galactopyranosyloxy-1H-imidazole-5-carboxamide.
8. 4-(2-acetamido-3,4,6-tri-O-acetyl-2-deoxy-β-D-glucopyranosyl)oxy-1H-imidazole-5-carboxamide.
9. 4-(2-acetamido-2-deoxy-β-D-glucopyranosyl)oxy-1H-imidazole-5-carboxamide.
10. 4-(2,3,4-tri-O-acetyl-α-L-rhamnopyranosyl)oxy-1H-imidazole-5-carboxamide.
11. 4-α-L-rhamnopyranosyloxy-1H-imidazole-5-carboxamide.
12. 4-(2,3,4,6-tetra-O-acetyl-α-D-mannopyranosyl)oxy-1H-imidazole-5-carboxamide.
13. 4-(3,4,6-tri-O-acetyl-2-deoxy-2-phthalimido-β-D-glucopyranosyl)oxy-1H-imidazole-5-carboxamide.
14. Methyl 1-O-(5-carbamoyl-1H-imidazole-4-yl)-2,3,4-tri-O-acetyl-β-D-glucopyranuronate.
15. Methyl 1-O-(5-carbamoyl-1H-imidazole-4-yl)-β-D-glucopyranuronate.
16. 1-O-(5-carbamoyl-1H-imidazole-4-yl)-β-D-glucopyranuronamide.
17. N-methyl[1-O-(5-carbamoyl-1H-imidazole-4-yl)-β-D-glucopyran]uronamide.
18. Ammonium 1-O-(5-carbamoyl-1H-imidazole-4-yl)-β-D-glucopyranuronate.
19. 4-(2,3,5-tri-O-benzoyl-α-D-arabinofuranosyl)oxy-1H-imidazole-5-carboxamide.
20. 4-α-D-arabinofuranosyloxy-1H-imidazole-5-carboxamide.
21. 4-(2,3,5-tri-O-acetyl-β-D-ribofuranosyl)oxy-1H-imidazole-5-carboxamide.
22. 4-β-D-ribofuranosyloxy-1H-imidazole-5-carboxamide.

* * * * *